United States Patent [19]

Berger

[11] Patent Number: 4,586,515
[45] Date of Patent: May 6, 1986

[54] DEVICE FOR MEASURING THE POSITION AND/OR MOTION OF A BODY PART

[76] Inventor: Meinhard Berger, A-6103 Reith 55, Austria

[21] Appl. No.: 567,402

[22] PCT Filed: Apr. 15, 1983

[86] PCT No.: PCT/AT83/00009
   § 371 Date: Dec. 16, 1983
   § 102(e) Date: Dec. 16, 1983

[87] PCT Pub. No.: WO83/03534
   PCT Pub. Date: Oct. 27, 1983

[30] Foreign Application Priority Data

Apr. 16, 1982 [AT] Austria .............................. A 1485/82

[51] Int. Cl.$^4$ .............................................. A61B 5/10
[52] U.S. Cl. ...................................................... 128/782
[58] Field of Search ........................ 128/782, 774, 779; 280/289 WC; 400/87; 350/321; 351/200, 209; 3/1.1; 273/190 A

[56] References Cited

U.S. PATENT DOCUMENTS

| | | | |
|---|---|---|---|
| 3,290,985 | 12/1966 | Bains et al. | 350/321 |
| 3,664,731 | 5/1972 | Jex | 351/200 |
| 3,769,636 | 11/1973 | Friedman | 3/1.1 |
| 4,306,571 | 12/1981 | McLeod | 128/782 |
| 4,320,766 | 3/1982 | Alihanka et al. | 128/782 |

FOREIGN PATENT DOCUMENTS

| | | | |
|---|---|---|---|
| 6889 | 8/1879 | Italy | 350/321 |
| 231711 | 4/1969 | U.S.S.R. | 128/782 |
| 562269 | 8/1977 | U.S.S.R. | 128/782 |

OTHER PUBLICATIONS

"A Variable Axis Electrogoniometer for the Measurement of Single Plane Movement", by J. Tata et al, J. Biomechanics, vol. 11, pp. 421–425.

Primary Examiner—Kyle L. Howell
Assistant Examiner—David Shay
Attorney, Agent, or Firm—Karl F. Ross; Herbert Dubno

[57] ABSTRACT

In the diagnostic evaluation of the measurement of head rotations for the functional examination of the cervical portion of the spine and the upper dorsal column it is to be noted that the head rotates not only with reference to that axial system which corresponds to the measuring system arranged between the holder and the supporting device, but also performs a three-dimensional movement in space. When tilting the head, e.g., the same not only rotates about a horizontal, frontal axis (parallel ear-to-ear) but also moves forward and downward. Even more complex are rotary or lateral tilting movements of the head which, beyond a certain extend of displacement, proceed only with a three-dimensional motion of the head. Yet the rotations of the head in a broader sense, including the ancillary movements referred to, are what permits more accurate conclusions as to the function of the spine. Analogous conditions apply to other sequences of movement with multijointed motion progressions, e.g. of the extremities.

It is therefore essential to the invention that not only the rotary movements of the holder are measured by the measuring system arranged between the holder and the supporting device but that also the motion of this measuring system or the holder in space is taken into consideration in the measurement or in the evaluation of the measuring results. This can be done, preferably, by an additional measuring system arranged, say, in the region of the supporting device for detecting the movements of the holder in space and/or mathematically in the evaluation by a data processor.

9 Claims, 5 Drawing Figures

DEVICE FOR MEASURING THE POSITION AND/OR MOTION OF A BODY PART

CROSS REFERENCE TO RELATED APPLICATION

This application is a national phase application of PCT/AT83/00009 filed Apr. 15, 1983 and based upon an Austrian application A 1485/82 filed Apr. 16, 1982 under the International Convention.

FIELD OF THE INVENTION

The invention relates to a device for measuring the position and/or motion of a body part, i.e. at least its rotation relative to another body part, consisting of a holder to be connected with the body part, a space-referenced supporting device for the holder and a measuring system consisting of measuring sensors for detecting the rotary movements of the holder with reference to the supporting device.

BACKGROUND OF THE INVENTION

For examinations, especially in fields of orthopedics and neuro-orthopedics which deal with functional disorders of the motor system, it is important to determine by measurement and to evaluate diagnostically certain positions and movements of body parts. For example, conclusions as to the function of the cervical portion of the spine and the upper dorsal column are possible through registration of the position and motion of the head. Functional disorders of these spinal regions are the most common cause for aches of the upper torso, arms and head. Even though static analyses can be carried out with present-day examination procedures (X-ray, scanning, etc.), an examination of the dynamics and function of the spine is only very limitedly realizable. Both the technique of this procedure and the radiation exposure set narrow limits for functional tests of the spine. A three-dimensional recording of the position of the head is possible with optical checking processes (film, video), but only with utilization of complex machinery and for specific functions.

For measuring head movements, there has already been made known (U.S. Pat. Nos. 3,161,846 and 3,290,935) a device of the kind initially set forth which, however, is not suited for diagnostic purposes since the free mobility of the head is excessively restricted so that diagnostically significant final positions of the head movements and rapid movements are not detectable. Furthermore, the known device does not give the physician access to the head to the extent necessary for diagnostic purposes.

OBJECT OF THE INVENTION

It is therefore the object of the invention to provide an improved device for measuring the position and/or motion of the head or other body parts which satisfies the diagnostic requirements.

SUMMARY OF THE INVENTION

This is achieved in accordance with the invention in that the holder is connected with the supporting device by means of a single articulated linkage in the region of which the measuring system is also disposed.

The invention is based upon the realization that, especially for the functional examination of the cervical portion of the spine and upper dorsal column, essential diagnostic data can be derived from the measurement of the rotation of the head. But also in other cases rotary movements of certain body parts, e.g. of the upper arm, the hand, the foot etc., may provide useful diagnostic information in a space-oriented coordinate system. The device according to the invention conforms to the diagnostic requirements especially in that it guarantees the freest possible mobility of the body part to be measured, with low mass inertia, in order to enable the detection of rapid movements as well as of the final positions of the body part and also to avoid those reactions of the measuring device upon the motion of the body part which may cause reflectionally induced changes of motion and thereby falsify the diagnostic results of the measurement. Besides, the physician's access to the body part, which may become sometimes necessary during the measuring procedure, is insured in that the connection between the holder and the supporting device is practically concentrated in single point (namely, that of the one articulated linkage).

Preferably the articulated linkage between the holder and the supporting device is effected through the measuring system itself, which preferably consists of at least three rotary measuring sensors forming a kinematic chain whose axes of rotation define a three-dimensional axial system.

The kinematic chain of the rotary measuring sensors can be advantageously so constructed that the rotary measuring sensors are arranged in series, in such a manner that one operating portion of the first rotary measuring sensor is connected with the holder, the other operating portion of the first rotary measuring sensor is connected with an operating portion of the second rotary measuring sensor, and so forth.

So-called rotary transmitters may be used as measuring sensors in the context of the device according to the invention. Rotary transmitters serve for the transformation of a measured variable, present as a rotary motion, into a variable suitable for electrical processing, such as resistance, current, voltage or the like. As an example of a suitable rotary transmitter the rotatable potentiometer (a resistive rotary transmitter) can be named.

Other rotary transmitters (e.g. inductive or capacitive) or else digital angle coders (optical, magnetic) may also be used as measuring sensors instead of rotatable potentiometers.

BRIEF DESCRIPTION OF THE DRAWING

The invention will be explained hereinafter in greater detail with reference to the drawing. In the drawing.

SPECIFIC DESCRIPTION

Figure 1:
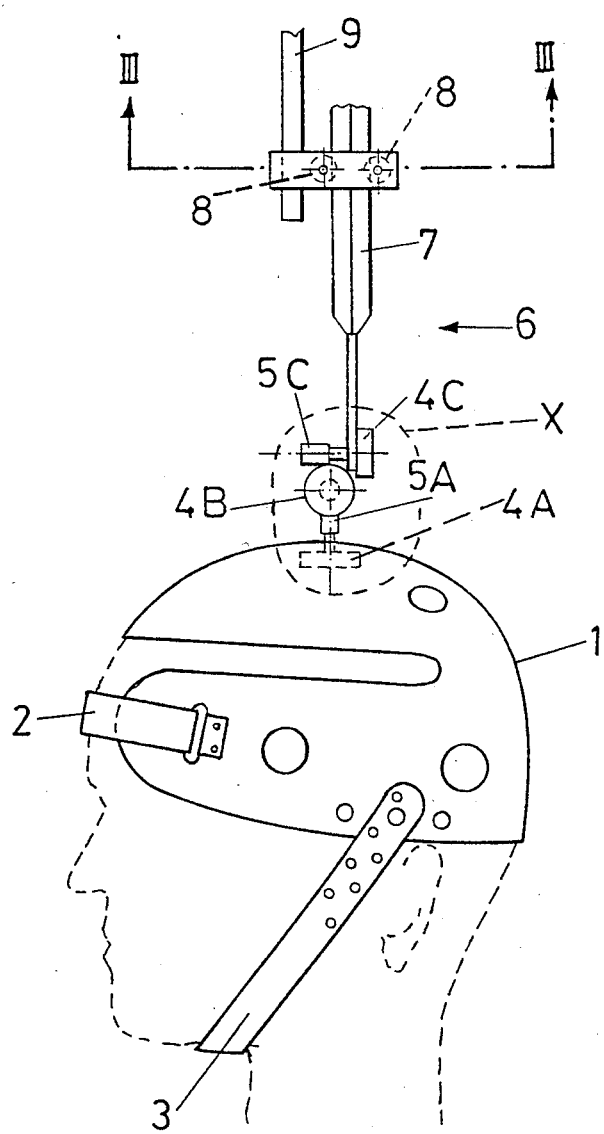
FIG. 1 is a side-elevational view of a measuring device according to the invention.
Figure 2:
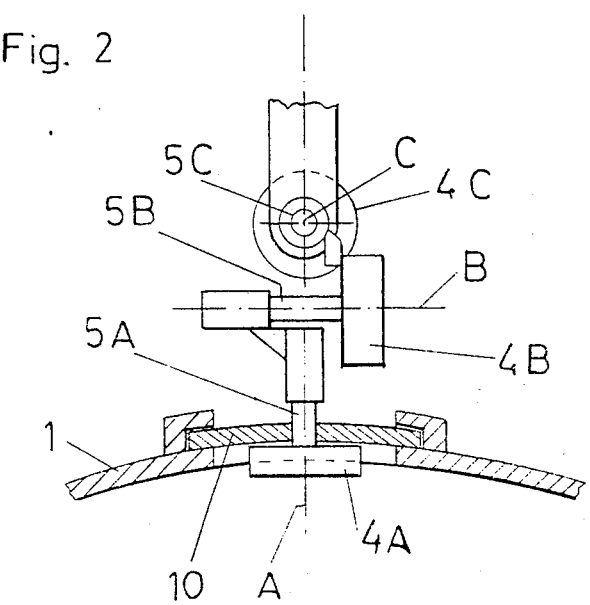
FIG. 2 is a front-elevational view of this measuring device for measuring the movement of the head.
Figure 3:
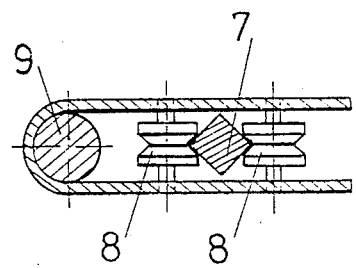
FIG. 3 is a sectional view taken along line III—III of FIG. 1.

FIGS. 1-4 show a device for measuring the position and motion of the head about three axes for a functional examination of the cervical portion of the spine, the upper dorsal column and functionally associated structures.

According to the illustrated embodiment, the holder to be connected with the body part consists of a helmet 1, made of a synthetic material, which can be adapted to the various head sizes and shapes by means of an adjustable head strap 2 and chin strap 3. On the upper surface of the helmet there is present, as a measuring system X, an arrangement of three rotatable potentiometers whose axes A, B, C, illustrated in FIGS. 1 and 2 in their starting (zero) position, are relatively offset by 90°. The housing 4A of the lowermost potentiometer is secured to helmet 1; its shaft 5A lies in axis A. The shaft 5B of the second potentiometer is rigidly connected with the shaft 5A of the first potentiometer and lies in axis B. The housing 4B of the second potentiometer is rigidly connected with the shaft 5C of the third potentiometer lying in axis C. The housing 4C of the third potentiometer is fixedly connected with the supporting device 6. The measuring system X constitutes, at the same time, also the sole articulated linkage between the holder (helmet 1) and the supporting device 6.

An adjusting plate 10, which is directly attached to the potentiometer housing 4A and which is displaceable in the sagittal plane relatively to helmet 1, is provided in a recess of helmet 1 for adjusting the first potentiometer 4A–5A with reference to helmet 1.

The supporting device 6 consists of a light-metal support bar 7 of rectangular profile. The support bar 7 is vertically freely movable in a weight-relieved mode, yet is nonrotatably disposed with reference to its vertical axis. The support bar 7 is guided on a guide boar 9 by rollers 8. The guide bar 9 is attached by means of a hinge to the ceiling of the examining room in such a manner that small pendular motions of the guide bar 9, and therefore of the support bar 7, are possible but no rotary movement of the support bar 7 about its longitudinal (here about vertical) axis. As can be seen from FIG. 4, the longitudinal displacement of support bar 7 relative to the guide bar 9 can also be measured, e.g. by a linear potentiometer 11, 12 whose movable operating element 11 is connected with the support bar 7 and whose housing 12 is attached to the guide bar 9 by lugs 13. Furthermore, the angular deflection of guide bar 9 can also be measured, namely, according to FIG. 4, by two potentiometers 14E–15E and 14F–15F which simultaneously constitute the articulated linkage between the guide bar and the ceiling 17. The housing 14E of one potentiometer is connected with the end of the guide bar 9. The shaft 15E of this potentiometer and the shaft 15F of the other potentiometer are rigidly interconnected. The housing 14F of the other potentiometer is attached to the ceiling 17 by means of an angle bracket 16. The articulated linkage of the guide bar 9 with the ceiling 17 permits swings of the guide bar 9 about the axes E and F.

The measured variables (angles of rotation) of the head movements about the three axes A, B, C are transformed by the three potentiometers of measuring system X into an output variable (resistive rotary transmitter) in an electrical resistance. The output variables of each of the three potentiometers are fed as electrical signals to a display apparatus (e.g. oscilloscope), a recording device (oscillograph) and/or a data processor, wherein the measuring signals coming from the individual potentiometers may be indicated or electronically processed either separately or in combination, i.e. in superposition. The display, recording and/or data-processing apparatus may also receive the output variables of the additional measuring sensors in or on the supporting device 6, either for the separate indication or for processing as corrective parameters for the rotary measurements. Transverse movements of the holder (helmet 1), which necessarily accompany the rotary movements as secondary motions, amy thus be exactly detected by the measuring device.

The measuring device described and illustrated in FIGS. 1–4 is used in the following manner:

The patient sits leaning back in the chair and holds his head upright. The helmet 1 is so mounted on the head that the three potentiometers form a three-dimensional axial system with their axes offset by 90° in the zero position. Axis A is vertically oriented along the longitudinal body axis. Axis B is horizontal and sagittal in the zero position; axis C is also horizontal, but frontal (parallel ear-to-ear). Rotation, flection and lateral tilting of the head are detected by the described measuring device, axis A remaining body-part-oriented (i.e. head-oriented) and axis C remaining space-oriented during the measuring process. Axis B is still space-oriented (together with axis C) upon a mere rotation of the head about axis A but becomes body-part-oriented (together with axis A) upon a mere lateral tilting of the head.

Figure 4:
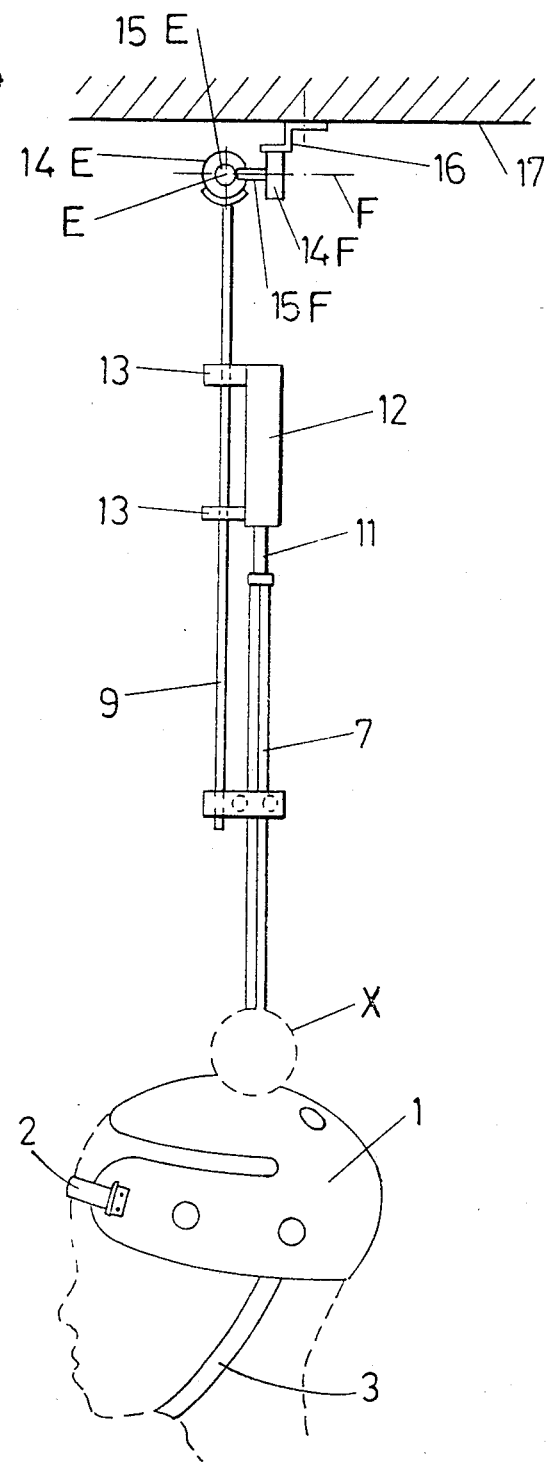
FIG. 4 is an overall view of the measuring device showing additional details of the supporting device.

Space-oriented does not necessarily means spatially fixed since the space-oriented axis C of the third potentiometer can carry out ancillary motions corresponding to the head movements on account of the articulated suspension of the guide bar 9 and the essentially vertical mobility of the support bar 8, yet always remaining in the vertical plane corresponding to the sagittal plane of the zero position. The relatively minor ancillary motions of axis C do not significantly affect the test result and could furthermore be compensated in a data processor, especially if, as can be seen in FIG. 4, the deflections and variations in length of the supporting device are measured, for example, by the potentiometers 11–12, 14E–15E, 14F–15F or other measuring sensors.

By the measuring process performed with the aid of the described device, the extent of movement of the upper cervical spine and dorsal column may be registered through end-position rotation, flection and extension as well as lateral tilting of the head. Furthermore, the dynamic progression of these movements can be exactly registered by slow and rapid back-and-forth rotation or flection and lateral tilting. Since the mechanics of the joints of the upper spinal portions prevent movements in only one plane, i.e. only multidimensional movements can occur, the registration of the synkiness (combination of rotation, lateral tilting and flection) is extremely important for the diagnosis of spinal disorders. Conclusions as to muscular tone, injury-related inhibition as well as nervous disturbances of the musculature (e.g. Parkinsons' disease, post-paralysis condition etc.) may be obtained from measurement of the angular velocity and the frequency of repeated movements. The mobility of certain portions of the upper cervical spine may be selectively tested and registered by fixation of individual vertebrae.

The possibility of installing a fourth potentiometer should be mentioned as another modification of the measuring device according to FIGS. 1–4. As can be seen from FIG. 5, this could be positioned e.g. between the third potentiometer 4C–5C and the support bar 7 in such a manner that the axis D of the fourth potentiometer lies in the essentially vertical axis of the support bar 7 and the housing 4D of the fourth potentiometer is fixedly connected with the support bar 7 while the shaft 5D of the fourth potentiometer is rigidly secured to the shaft 5C of the third potentimeter. The axes D and A of the fourth and the first potentiometer coincide in the zero position.

Either the first or the fourth potentiometer must be blocked during measuring (i.e. the shaft must be immobilized with reference to the housing). With blocking of the first potentiometer the vertical axis D remains space-oriented whereas the horizontal axis B remains body-part-oriented (head-oriented) during the measurement.

Figure 5:
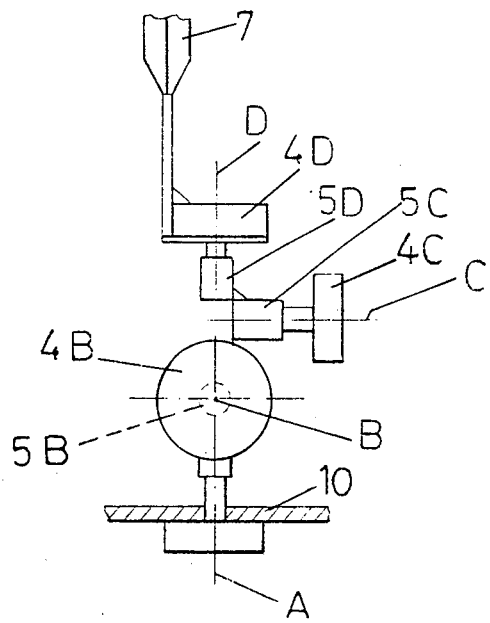
FIG. 5 is a side-elevational view of a modified version of FIG. 1.

A possible modification of the potentiometer arrangement of FIG. 5 resides in omitting the lowermost potentiometer and connecting instead potentiometer 4B-5B with the helmet or with the adjusting plate 10.

Even though the essence of the device according to the invention concerns the measurement of rotary movements of body parts, it is of course also possible to measure transverse movements of the body parts in connection therewith, with the measuring results of the rotary and transverse movements displayed, recorded or electronically processed either separately or in combination with the measuring results of the rotary movements.

I claim:

1. A method for the diagnosis of nuerological and orthopedic motion disorders of a body part which comprises the steps of:
    affixing to said body part a single articulation consisting of three rotary displacement sensors having mutually orthogonal axes and each consisting of two relatively rotatable members defining the respective axis such that a first member of a first of said sensors is rigidly connected to said body part, a second member of said first sensor is rigidly connected to a first member of a second of said sensors, a second member of said second sensor is rigidly connected to a first member of a third of said sensors and a second member of said third sensor is rotatable relative to said first member of said third sensor about an axis of said third sensor;
    spacially positioning said second member of said third sensor by fixing it against rotation but enabling linear displacement of said second member of said third sensor while permitting pendular displacement of said axis of said third sensor with respect to a reference point in space about two pendular axes neither of which is parallel to said linear displacement of said second member;
    measuring linear displacement of said second member of said third sensor with a fourth motion sensor;
    measuring angular displacement of said axis of said third sensor about said reference point with fifth and sixth motion sensors respectively responsive to displacement about said pendular axis; and
    causing said body part to move and detecting outputs of said sensors as an indication of the motion pattern of said body part in space to a diagnose a motion disorder.

2. An apparatus for the diagnosis of neurological and orthopedic motion disorders of a body part which comprises:
    a holder adapted to be affixed to a body part, motion of which is to be monitored for diagnosis of a neurological or orthopedic motion disorder;
    a sensing system forming a single three-axis articulation affixed to said holder, said sensing system comprising:
        three rotary displacement sensors having mutually orthogonal axes and each consisting of two relatively rotatable members defining the respective axis,
        a first member of a first of said sensors being rigidly connected to said holder,
        a second member of said first sensor being rigidly connected to a first member of a second of said sensors,
        a second member of said second sensor being rigidly connected to a first member of a third of said sensors and a second member of said third sensor being rotatable relative to said first member of said third sensor about an axis of said third sensor;
    a longitudinally shiftable support element connected to said second member of said third sensor and restricting angular displacement of said second member of said third sensor while guiding said sensing means linearly with respect to a reference point spaced from said holder;
    means for mounting said support element to permit pendular displacement of said support element about two different pendular axes neither of which are parallel to the linear displacement of said element with respect to said reference point;
    a fourth sensor responsive to linear displacement of said sensing system in the direction of said linear displacement; and
    fifth and sixth sensors respectively responsive to angular displacement of said element about said pendular axes whereby outputs of said sensors can be monitored to provide an indication of motion disorders of a body part engageable in said holder.

3. The apparatus defined in claim 2 wherein said rotary displacement sensors are rotary potentiometers.

4. The apparatus defined in claim 3 wherein said holder is a helmet which can receive a head of a patient having a motion disorder to be diagnosed and each of said potentiometers has a housing and a shaft, a housing of a first potentiometer forming said first sensor being connected to said helmet, the shaft of said first potentiometer being connected to the shaft of a second potentiometer forming said second sensor, the housing of said second potentiometer being connected to the shaft of a third potentiometer forming said third sensor, and the housing of said third potentiometer being fixed to said element.

5. The apparatus defined in claim 3 wherein the shaft of a first potentiometer forming said first sensor is connected to said helmet, the housing of said first potentiometer is connected with the shaft of a second potentiometer forming said second sensor, the housing of said second potentiometer being connected to the shaft of a third potentiometer forming said third sensor and the housing of said third potentiometer being connected to said element.

6. The apparatus defined in claim 5, further comprising a fourth potentiometer having a shaft connected with the shaft of said third potentiometer and a housing connected with said element, one of said first and fourth potentiometers having its shaft arrestable with respect to the respective housing.

7. The apparatus defined in claim 2 wherein said element is a rod freely vertically movable in a weight-relieving mode.

8. The apparatus defined in claim 7, further comprising means for guiding said rod while preventing rotation thereof.

9. The apparatus defined in claim 2 wherein said fourth, fifth and sixth sensors form a kinematic chain articulating said element about said reference point.

* * * * *